(12) United States Patent
Kamitakahara et al.

(10) Patent No.: US 8,003,611 B2
(45) Date of Patent: Aug. 23, 2011

(54) COMPOSITE MATERIAL USEFUL AS BIOMATERIAL AND ITS PREPARATION

(75) Inventors: Masanobu Kamitakahara, Ikoma (JP); Masao Tanihara, Ikoma (JP); Chikara Ohtsuki, Ikoma (JP); Shinichi Ogata, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 978 days.

(21) Appl. No.: 11/886,318

(22) PCT Filed: Mar. 14, 2006

(86) PCT No.: PCT/JP2006/305035
§ 371 (c)(1), (2), (4) Date: Oct. 10, 2007

(87) PCT Pub. No.: WO2006/098326
PCT Pub. Date: Sep. 21, 2006

(65) Prior Publication Data
US 2009/0005881 A1 Jan. 1, 2009

(30) Foreign Application Priority Data
Mar. 15, 2005 (JP) .................. 2005-072792

(51) Int. Cl.
*A61K 38/17* (2006.01)
(52) U.S. Cl. ....... 514/17.2; 530/324; 530/325; 530/326; 530/327; 530/328; 530/356
(58) Field of Classification Search .................. None
See application file for complete search history.

(56) References Cited

OTHER PUBLICATIONS

Tanihara et al. JP2005-58499. Publication date Mar. 10, 2005. Machine assisted English translation.*
L. L. Hench et al., An Introduction to Bioceramics, pp. 1-24, World Scientific, NY, 1993.
L.L. Hench et al., "Bonding Mechanism at the Interface of Ceramics Prosthetic Materials", Journal of Biomedical Materials Research, vol. 2, (Part 1), pp. 117-141, 1971.
M. Jarcho et al., "Tissue, Cellular and Subcellular Events at a Bone-Ceramic Hydroxylapatite Interface", Journal of Bioengineering, vol. 1, pp. 79-92, 1977.
M. Neo et al., "Apatite Formation on Three Kinds of Bioactive Material at an Early stage in vivo: A Comparative Study by Transmission Electron Microscopy", Journal of Biomedical Materials Research, vol. 27, pp. 999-1006, 1993.

* cited by examiner

*Primary Examiner* — Anish Gupta
(74) *Attorney, Agent, or Firm* — Wenderoth, Lind & Ponack, L.L.P.

(57) ABSTRACT

The present invention aims at providing a biomaterial composite not having risks of pathogen infection and unfavorable side effects such as rejection response. According to the invention, there is provided a biomaterial composite, which comprises a polypeptide and a calcium phosphate compound, said peptide comprising the units of Formulas (I) to (III):

$$[-(OC-(CH_2)_m-CO)_p\text{-}(Pro\text{-}Y\text{-}Gly)_n-]_a \quad (I)$$

$$[-(OC-(CH_2)_m-CO)_q\text{-}(z)_r-]_b \quad (II)$$

$$[-HN-R-NH-]_c \quad (III)$$

wherein m, p, q, Y, n, Z, r, R, a, b and c are as defined in the specification. The composite of the invention is particularly suitable for an artificial bone due to its high biocompatibility, high endurance and mechanical strength. Further, the invention can provide a process of the composite according to the invention can for preparation of the composite having excellent mechanical characteristics by a simple procedure.

17 Claims, 8 Drawing Sheets

Figure 1

The surface of an artificial collagen soaked in 1.5SBF(pH 7.40)
(taken by digital microscope)

Figure 2

The photograph of the surface of an artificial collagen soaked in 1.5SBF (pH 7.40) for 7 days, taken by scanning electron microscope (SEM)

Figure 3

A chart showing thin-film X-ray diffraction patterns of an artificial collagen film before and after soaking in 1.5 SBF

Figure 4

A chart showing analysis of a film before and after soaking by energy dispersive X-ray spectrometer

Figure 5

A photograph of the surface of a porous body before soaking taken by SEM

Figure 6

EDX spectrum of a porous body before soaking

Figure 7

A photograph of the surface of a porous body after soaking taken by SEM

EDX spectrum of a porous body after soaking

COMPOSITE MATERIAL USEFUL AS BIOMATERIAL AND ITS PREPARATION

This application is a U.S. national stage of International Application No. PCT/JP2006/305035 filed Mar. 14, 2006.

TECHNICAL FIELD

The present invention relates to a composite material useful as a biomaterial comprising a chemosynthetic collagen and a calcium phosphate compound and a process for preparing the composite material. The biomaterial or biomaterial composite of the present invention is a bio-compatible hard tissue composite material having a composition analogous to a material from a living body, and its shaped article is used as an artificial bone or the like.

BACKGROUND ART

Known biomaterials comprising inorganic materials, which may be implanted to a living body, can bond directly to bones but are defective in being friable and too high in elasticity compared with natural bones (cf. Non-patent Literatures 1 to 4). Known biomaterials comprising only organic materials do not bond directly to bones, are weak in strength and do not produce adhesion to the surrounding tissues, whereby the rebuilding of the tissues such as bones in a living body is delayed in the inductive tissue regeneration method.

In order to solve the above problems, it is proposed, for instance, in JP-A-7-101708 (Patent Literature 1) to provide a biomaterial composite (e.g. a composite of apatite as the inorganic material and collagen as the organic material) in a shaped form having physical properties analogous to bones in a living body, said biomaterial composite being prepared by adding a collagen solution admixed with phosphoric acid gradually to a suspension of calcium hydroxide, collecting the deposited material by filtration and drying the collected material, followed by compression molding.

Since the biomaterial composite as proposed above has a Young's modulus to the same extent as soft bones, it is further proposed in JP-A-11-199209 (Patent Literature 2) to provide an improved biomaterial composite of collagen and a calcium phosphate compound having a Young's modulus to the same extent as hard bones, said improved biomaterial composite being prepared by dropwise addition of an aqueous phosphoric acid solution containing collagen and an aqueous solution containing a calcium salt simultaneously to a reaction vessel and compression molding of the deposited material.

This collagen/calcium phosphate composite has physical properties similar to bones in a living body and is a biomaterial having excellent characteristics in bone substitution, tissue reconstruction, strength, etc. However, it has a problem in becoming friable with the lapse of time after implantation in a living body to degrade finally. To solve this problem, it is proposed in JP-A-2001-276207 (Patent Literature 3) to use a cross-linking agent in either on or after the compression step in the preparation of a collagen/calcium phosphate composite so as to make such composite cross-linked whereby the resistance to degradation on the implantation in a living body is enhanced while keeping a sufficient strength.

On the other hand, M. Neo et al. have studied and reported on the reaction between bioactive ceramics (indicating inorganic materials capable of binding to bones directly) and bones. According to such report, the implantation of a crystallized glass A-W in a rat tibia for 2 weeks resulted in formation of a hydroxyapatite layer on the surface of said glass by its reaction with body fluid. Thus, bones (cells) do not recognize the glass-hydroxyapatite composite as a xenobiotic (cf. Non-patent Literature 4).

Patent Literature 1: JP-A-7-101708;
Patent Literature 2: JP-A-11-199209;
Patent Literature 3: JP-A-2001-276207;
Patent Literature 4: JP-A-2003-321500;
Non-patent Literature 1: L. L. Hench and J. Wilson, "An Introduction to Bioceramics", World Scientific Publishing Co. Pte. Ltd, Singapore, 1993, pp. 1-24;
Non-patent Literature 2: L. L. Hench, R. J. Splinter, W. C. Allen and T. K. Greenlee, Journal of Biomedical Materials Research, 1971, Vol. 2, p. 117-141, "Bonding Mechanism at The Interface of Ceramics Prosthetic Materials";
Non-patent Literature 3: M. Jarcho, J. L. Kay, R. H. Gumaer and H. P. Drobeck, Journal of Bioenergetics, 1977, Vol. 1, p. 79-92, "Tissue, Cellular and Subcellular Events at Bone-ceramic Hydroxyapatite Interface";
Non-patent Literature 4: M. Neo, T. Nakamura, C. Ohtsuki, T. Kokubo and T. Yamamoto, Journal of Biomedical Materials Research, 1993, Vol. 27, p. 999-1006.

DISCLOSURE OF INVENTION

Problem to be Solved by Invention

Since collagens used in the above patent and Non-patent Literatures are originated from animals such as cow and pig, the implantation of artificial bones prepared from such collagens into human may cause such a risk as infection with pathogens or unfavorable side effects (e.g. rejection response) (cf. Masao Tanihara, FRAGRANCE JOURNAL, July 2004, "Chemical Synthesis of Collagens with Amino Acids"). To overcome such risk, the use of a chemo-synthetic collagen instead of a natural collagen from animal may be considered. For practical application of artificial bones formed with a composite comprising a chemosynthetic collagen and a calcium phosphate compound, however, various tests are required, for instance, on whether the composite has physical properties analogous to living bones and favorable characteristics as biomaterials in bone substitution, tissue reconstruction, strength, etc., whether the composite is neither friable with the lapse of time nor broken, whether the composite is not recognized as a xenobiotic to cause any unfavorable effect, etc.

Measures to Solve Problem

As a result of the extensive study, it has been found that a biomaterial composite obtained from a certain chemosynthetic collagen and a calcium phosphate compound has a satisfactory property practically applicable as an artificial bone. The present invention is based on such finding.

Effect of Invention

The present invention provides a biomaterial composite not having such a risk as infection of pathogens and undesired side effects. The present invention also provides a composite different from the one prepared with natural collagen in thermostability, degradative rate and/or cell adhesion, said composite being prepared by the use of a chemosynthetic collagen having a non-natural sequence and a calcium phosphate compound. Since the composite of the present invention has high biocompatibility as well as high endurance and mechanical strength, it is particularly suitable for an artificial bone. Further, the process for preparation of the composite according to the present invention can afford the one excellent in mechanical properties by a simple procedure.

BEST MODE FOR CARRYING OUT INVENTION

In an aspect of the present invention, it provides a biomaterial composite (hereinafter referred to as "a composite of the invention"), which comprises a polypeptide (random polymer) and a calcium phosphate compound, said polypeptide comprising the units of Formulas (I) to (III);

(I)

(II)

(III)

[wherein
m is an integer of 1 to 18;
p and q are each independently 0 or 1;
a is an integer of 1 to 10,000 and b and c are each independently an integer of 1 to 10,000;
each Ys is independently Pro, Hyp or a group of the formula:

wherein R' is H or C1-6 alkyl and X is a divalent group;
n is an integer of 1 to 20;
Z is an amino acid residue or peptide chain consisting of 1 to 10 amino acid(s);
r is an integer of 1 to 20;
R is a straight or branched chain alkylene group of 2 to 12 carbon atoms;
the molar ratio of a and b (a/b) is 100/0 to 30/70;
when p is 1 and q is 0, c equals to a;
when p is 0 and q is 1, c equals to b;
when p is 1 and q is 1, c equals to a+b; and
when p is 0 and q is 0, c is 0].

In the above formula, a is, for example, an integer of 1 to 10,000; b is, for example, 0 to 10,000; and c is, for example, 0 to 10,000.

The composite of the invention is preferred to have Z, which is an amino acid residue or peptide chain consisting of one or more amino acids selected from Gly, Sar, Ser, Glu, Asp, Lys, His, Ala, Val, Leu, Arg, Pro, Tyr and Ile.

The composite of the invention is also preferred to have p, q and c, which are each 0.

More preferably, Z is an amino acid residue or peptide chain selected from Gly, Sar, Ser, Glu, Asp, Lys, Arg-Gly-Asp, Tyr-Ile-Gly-Ser-Arg, Ile-Lys-Val-Ala-Val, Val-Pro-Gly-Val-Gly, Asp-Gly-Glu-Ala, Gly-Ile-Ala-Gly, His-Ala-Val, Glu-Arg-Leu-Glu, Lys-Asp-Pro-Lys-Arg-Leu and Arg-Ser-Arg-Lys.

Particularly preferred is the complex of the invention wherein each of Ys is independently Hyp or a group of the formula:

wherein R' is H or C 1-6 alkyl and X is a divalent group.

More preferred is the composite of the invention which comprises a polypeptide and a calcium phosphate compound, said polypeptide comprising the units of the formula (I'):

H-(Pro-Y-Gly)$_s$-OH  (I')

wherein
s is integer of not less than 10;
each of Ys is Hyp or a group of the formula:

wherein R' is H or C 1-6 alkyl and X is a divalent group. In the above formula, s is, for example, 10 to 200,000.

Preferably, Y in the above formula is a group of the formula:

wherein R' is H or C1-6 alkyl and X is a divalent group. More preferably, the divalent group is —CONHC$_{1-6}$ alkyl or —C$_{1-6}$ alkyl(OH)CH$_2$OC$_{1-6}$ alkyl-, especially —CONHCH$_2$—, —CONHCH$_2$CH$_2$—, —CONHCH$_2$CH$_2$CH$_2$—, —CONHCH$_2$CH$_2$CH$_2$CH$_2$—, —CH$_2$CH(OH)CH$_2$O—, —CH$_2$CH(OH)CH$_2$OCH$_2$—, —CH$_2$CH(OH)CH$_2$OCH$_2$CH$_2$— or —CH$_2$CH(OH)CH$_2$OCH$_2$CH$_2$CH$_2$—.

In the composite of the invention, Ys in two different peptide units may be combined together to form a siloxane bond.

In another aspect of the present invention, it provides a polypeptide comprising the units of Formulas (I) to (III):

$$[-(OC-(CH_2)_m-CO)_p\text{-(Pro-Y-Gly)}_n-]_a \quad (I)$$

$$[-(OC-(CH_2)_m-CO)_q\text{-}(z)_r\text{-}]_b \quad (II)$$

$$[-HN-R-NH-]_c \quad (III)$$

wherein
m is an integer of 1 to 18;
p and q are each independently 0 or 1;
a is an integer of 1 to 10,000 and b and c are each independently an integer of 1 to 10,000;
each of Ys is independently a group of the formula:

wherein
R' is H or $C_{1-6}$ alkyl and X is a divalent group;
n is an integer of 1 to 20;
Z is an amino acid residue or peptide chain consisting 1 to 10 amino acid(s);
r is an integer of 1 to 20;
R is a straight or branched chain alkylene group of 2 to 12 carbon atoms;
the molar ratio of a and b (a/b) is 100/0 to 30/70;
when p is 1 and q is 0, c equals to a;
when p is 0 and q is 1, c equals to b;
when p is 1 and q is 1, c equals to a+b; and
when p is 0 and q is 0, c is 0. When the circular dichroism spectrum of each of the above polypeptides is determined at 10 to 80° C., there will be observed a positive cotton effect at 220 to 230 nm and a negative cotton effect at 195 to 205 nm, which suggests the formation of a triple-helical structure. This means that 3 said polypeptides form collagen-like fiber at their entire or parts.

In each of the above polypeptides, Ys in two different peptide units may be combined together to form a siloxane bond (—Si—O—Si—). The polypeptide cross-linked by the siloxane bond is understood to form also a triple-helical structure.

The term of "calcium phosphate compound" used in this specification represents a compound comprising Ca and $PO_4$, of which examples are $Ca_{10}(PO_4)_6(OH)_2$, $CaHPO_4$, $CaHPO_4 \cdot 2H_2O$, $\alpha\text{-}Ca_3(PO_4)_2$, $\beta\text{-}Ca_3(PO_4)_2$, $Ca_5(PO_4)_3OH$, $Ca_4O(PO_4)_2$, $Ca_{10}(PO_4)(OH)_2$, $Ca(PO_3)_2$, $Ca_2P_2O_7$, $Ca(H_2PO_4)_2$, $Ca(H_2PO_4)_2 \cdot H_2O$, $Ca_8H_2(PO_4)_6 \cdot 5H_2O$. From the viewpoint of a biocompatibility, a preferred calcium phosphate compound is hydroxyapatite, i.e. $Ca_{10}(PO_4)_6(OH)_2$, which may have lattice defects. The lattice defects mean partial deletion, substitution or the like Ca, $PO_4$ and/or OH. Examples of the chemical species by which Ca may be substituted are Na, K, Mg, etc., examples of the chemical species by which $PO_4$ may be substituted are $HCO_3$, $CO_3$, $HPO_4$, etc., and examples of the chemical species by which OH may be substituted are Cl, $HCO_3$, $CO_3$, etc.

In a further aspect of the present invention, it provides a method for preparing the composite of the invention, which comprises soaking a polypeptide in an aqueous solution of $CaCl_2$, preferably 0.001 to 5.0 M (e.g. 1.0 M) $CaCl_2$ solution, and then soaking the polypeptide in simulated body fluid (SBF) or conc. SBF to deposit a calcium phosphate compound on the surface of the polypeptide thereby the composition of the invention being obtained, said polypeptide comprising the units of Formulas (I) to (III)

$$[-(OC-(CH_2)_m-CO)_p\text{-(Pro-Y-Gly)}_n-]_a \quad (I)$$

$$[-(OC-(CH_2)_m-CO)_q\text{-}(z)_r\text{-}]_b \quad (II)$$

$$[-HN-R-NH-]_c \quad (III)$$

[wherein;
m is an integer of 1 to 18;
p and q are each independently 0 or 1;
a is an integer of 1 to 10,000 and b and c are each independently an integer of 1 to 10,000;
each of Ys is independently Pro, Hyp or a group of the formula:

wherein
R' is H or $C_{1-6}$ alkyl; and
X is a divalent group;
n is an integer of 1 to 20;
Z is an amino acid residue or peptide chain consisting 1 to 10 amino acid(s);
r is an integer of 1 to 20;
R is a straight or branched chain alkylene group of 2 to 12 carbon atoms;
the molar ratio of a and b (a/b) is 100/0 to 30/70;
when p is 1 and q is 0, c equals to a;
when p is 0 and q is 1, c equals to b;
when p is 1 and q is 1, c equals to a+b; and
when p is 0 and q is 0, c is 0].

The term "simulated body fluid (SBF)" refers to a solution containing an ion(s) with the molar concentration(s) as indicated in Table 1. Such ion concentration in SBF is nearly equal to that in human blood plasma, but difference is present between them in that human blood plasma contains 103.0 mM of $Cl^-$ and 27.0 mM of $HCO_3^-$. For promotion of the deposition of the calcium phosphate compound on the surface of the synthetic collagen, it is possible to use conc. SBF, e.g. a solution containing ions in which each ion has a concentration of 1.1 to 5.0 folds (e.g. 1.5 folds) that as shown in Table 1 with maintaining the relative proportion of the ion concentrations as given in said Table. The solution containing ions in 1.5 fold concentrations is called "1.5SBF" in this specification.

TABLE 1

| | Concentration (mM) | |
|---|---|---|
| Ions | SBF | 1.5 SBF |
| $Na^+$ | 142.0 | 213.0 |
| $K^+$ | 5.0 | 7.5 |
| $Mg^{2+}$ | 1.5 | 2.3 |
| $Ca^{2+}$ | 2.5 | 3.8 |
| $Cl^-$ | 147.8 | 221.7 |

TABLE 1-continued

| | Concentration (mM) | |
|---|---|---|
| Ions | SBF | 1.5 SBF |
| $HCO_3^-$ | 4.2 | 6.3 |
| $HPO_4^{2-}$ | 1.0 | 1.5 |
| $SO_4^{2-}$ | 0.5 | 0.8 |

In the process for preparing the composite of the invention, the temperature on soaking in an aqueous solution of $CaCl_2$ is not specifically limited insofar as the chemosynthetic collagen is not denatured and may be preferably from 10 to 80° C., more preferably from 20 to 40° C. The chemosynthetic polypeptide used in the present invention forms a triple-helical structure, and this structure is confirmed to be stable at a temperature of 10 to 80° C. by measurement of the circular dichroism spectrum. The temperature on soaking in SBF is also not specifically limited and may be preferably from 10 to 80° C., more preferably from 20 to 40° C. A longer time of soaking in SBF or the like and a higher concentration of conc. SBF result in precipitation of a larger amount of the calcium phosphate compounds. Soaking in SBF or the like for a long period of time, followed by exchange of SBF with a fresh one also increases the precipitated amount of the calcium phosphate compound. When desired, the composite of the invention as above obtained may be freeze-dried to make a porous article.

In the process for preparing the composite of the invention, there may be used, for instance, any one of Solutions 1 to 3 as shown in Table 2 instead of SBF or conc. SBF. The pH of SBF or conc. SBF, or of the Solution used instead of the same is within a range of 5 to 9, preferably of 7.2 to 7.5.

TABLE 2

| | Solution 1 | Solution 2 | (Unit: mM) Solution 3 |
|---|---|---|---|
| $Na^+$ | 150.0 | 132.0 | 170.0 |
| $K^+$ | 0.5 | 3.0 | — |
| $Mg^{2+}$ | 0.5 | 1.0 | 1.0 |
| $Ca^{2+}$ | 1.5 | 5.0 | 0.6 |
| $Cl^-$ | 103.0 | 132.2 | 157.0 |
| $HCO_3^-$ | 2.0 | 1.0 | 3.2 |
| $HPO_4^{2-}$ | 0.5 | 0.3 | 0.6 |
| $SO_4^{2-}$ | 0.1 | 0.2 | 1.0 |

In this specification, the term "chemosynthetic collagen" is used to mean a polypeptide synthesized chemically, which comprises the units of Formulas (I) to (III):

[wherein m is an integer of 1 to 18;

p and q are each independently 0 or 1;

each of Ys is independently Pro, Hyp or a group of the formula:

wherein R' is H or C1-6 alkyl and X is a divalent group;

n is an integer of 1 to 20;

Z is an amino acid residue or peptide chain consisting of 1 to 10 amino acid(s);

r is an integer of 1 to 20;

R is a straight or branched chain alkylene group of 2 to 12 carbon atoms;

the molar ratio of a and b (a/b) is 100/0 to 30/70;

when p is 1 and q is 0, c equals to a;

when p is 0 and q is 1, c equals to b;

when p is 1 and q is 1, c equals to a+b; and when p is 0 and q is 0, c is 0.

Details of the chemosynthetic collagen wherein Y is Pro or Hyp are disclosed in JP-A-2003-321500.

Briefly, the chemosynthetic collagen is prepared usually by condensing polypeptides respectively comprising the units of Formulas (I), (II) and (III):

[wherein m is an integer of 1 to 18;

p and q are each independently 0 or 1;

each of Ys is independently Pro or Hyp;

n is an integer of 1 to 20;

Z is an amino acid residue or peptide chain consisting of 1 to 10 amino acid(s);

r is an integer of 1 to 20;

R is a straight or branched chain alkylene group of 2 to 12 carbon atoms;

the molar ratio of a and b (a/b) is 100/0 to 30/70;

when p is 1 and q is 0, c equals to a;

when p is 0 and q is 1, c equals to b;

when p is 1 and q is 1, c equals to a+b; and when p is 0 and q is 0, c is 0]

in a solvent (water and/or an organic solvent) in the presence of a dehydrative condensing agent such as a carbodiimide condensing agent (e.g. diisopropylcarbodiimide (DIPC), 1-ethyl-3-(3-dimethylaminopropyl)carbodiimide (EDC), 1-ethyl-3-(3-dimethyl-aminopropyl)-carbodiimide hydrochloride (EDC.NCl), dicyclohexyl-carbodiimide (DCC)), a fluorophosphate condensing agent (e.g. O-(7-azabenzotriazol-1-yl)-1,1,3,3-tetramethyluronium hexafluorophosphate, O-benzotriazol-1-yl-N,N,N',N'-tetra-methyluronium hexafluorophosphate, benzotriazol-1-yl-oxy-trispyrrolidino phosphonium hexafluorophosphate, benzotriazol-1-yl-tris(dimethylamino)phosphonium hexa-fluorophosphide (BOP)) or diphenylphosphoryl azide, optionally in the coexistence of a condensation (or dehydration) aid such as N-hydroxy-polyvalent carboxylic acid imides, N-hydroxytriazoles (e.g. N-hydroxybenzo-triazoles, particularly 1-hydroxybenzotriazole), triazines or ethyl 2-hydroxyimino-2-cyanoacetate); and optionally (ii) soaking the thus condensed peptide in an organic solvent containing a silane coupling agent having a group of $-Si(OR')_3$ (wherein R' is as defined above) at the terminal (e.g. isocyanatopropyltriethoxysilane, glycidoxypropyl-trimethoxysilane), said organic solvent being preferred to be the one inert to the silane coupling agent and the chemosynthetic collagen such as toluene or THF, followed by hydrolysis.

In this specification, the term "C1-6 alkyl" refers to a straight or branched chain group of 1 to 6 carbon atoms and includes, for example, methyl, ethyl, n-propyl, isopropyl, n-butyl, tert-butyl, n-pentyl and n-hexyl.

The Si content in the polypeptide of the invention will be varied with various factors and may be dependent on the amount complexed with the calcium phosphate compound, the degradation rate of the composite in a living body, the use and configuration of the biomaterial, the reaction rate to the artificial collagen, etc. Thus, it will be varied within a range of 0 to 100%, preferably of 5 to 80%, more preferably of 10 to 50% on the basis of —OH in the artificial collagen.

The biomaterial composite of the present invention is excellent in bioaffinity or biocompatibility and may be used as a implant material such as an artificial bone, a dental implant, a bone reparative material, a bone filler, gnathic bone rebuilding material or an artificial joint fixation material. The composite of the invention may be used in the form of granule or bulk. When used in the form of granule, the particle size is preferred to be within a range of about 0.1 to 10 mm. When used in the form of bulk, the size is preferred to be nearly equal to that of the part to be applied.

When the biomaterial composite of the present invention is used as an artificial bone, the weight proportion of the polypeptide and the calcium phosphate compound may be from 1:9 to 9:1, preferably from 2:8 to 8:2. Since a living bone comprises about 30% by weight of collagen and about 70% by weight of apatite, the weight proportion of the polypeptide and the phosphate calcium compound for the artificial bone is preferably adjusted to about 3:7 so as to have a strength analogous a living bone. Also, the artificial bone may be prepared by the use of the biomaterial composite having a content of the calcium phosphate compound of about 1 to 90% by weight, preferably of 10 to 90% by weight, more preferably of 25 to 75% by weight so as to have a compatibility to the bone cells.

After the composite of the invention is implanted into a living body, a new bone will grow on the surface of said composite to ossification. Since the composite of the invention has a layer of the calcium phosphate compound and is not recognized as a xenobiotic, it is compatible to bones and useful as a biomaterial, for example, to make an artificial bone.

In another aspect of the present invention, the composite may include, for example, one or more physiologically or pharmacologically acceptable active components, excipients, additives or the like. Examples of the active component are disinfectants, antiseptics, anti-inflammatory agents, antiphlogistics analgetics, anti-itch agents, anti-ulcer agents, anti-allergic agents, anti-virus agents, anti-mycotic agents, antibiotics, emollients, decubitus/dermal therapeutic agents, vitamins, Chinese drugs, etc. Examples of the active component may be also one or more hemostatic agents (e.g. fibrin as a blood clotting factor), polypeptides or their salts having cellular proliferation promoting activity, angiogenic activity and/or cell adhesive activity.

If necessary, the composite of the invention may comprise an acid component such as acetic acid, citric acid, tartaric acid or malic acid, or a base component such as an inorganic base comprising ammonium base, sodium base, potassium base, magnesium base or calcium base or an organic base chosen from triethylamine base, ethanolamine base, triethanolamine base, etc.

The biomaterial or medical material may be a composite of the polypeptide (or a composition comprising the polypeptide) and an organic or inorganic base material. Usually, the base material may have bioaffinity or biocompatibility.

Examples of the inorganic base material are metal oxides such as silica, zirconia or titania, calcium phosphate such as hydroxyapatite, metals such as aluminum, stainless steel, titanium or titanium alloy and ceramics.

Examples of the organic base material are polysaccharides or their derivatives (e.g. alginate, chitin, chitosan, hyaluronic acid, polygalactosamine, curdlan, pullulan, xanthan, dextran), cellulose ethers (e.g. cellulose, methylcellulose, ethylcellulose, carboxymethylcellulose or its salts, hydroxyethylcellulose, hydroxypropylcellulose, hydroxypropylmethylcellulose), cellulose esters (e.g. cellulose acetate), proteins (e.g. gelatin, casein, albumin), polypeptides (e.g. polylysine, polyglutamine, polyglutamic acid), vinyl alcohol resins (e.g. polyvinyl alcohol resin, ethylene-vinyl alcohol copolymer), polyvinyl pyrrolidone resins, acrylic resins (e.g. poly(methylmethacrylate) polymer), halogen-containing resins (e.g. fluorinated resin such as polytetrafluoroethylene, vinyl chloride resin such as polyvinyl chloride), polyurethane resins, silicone resins, polyester resins, polyamide resins (e.g. nylon 6, nylon 66), etc.

The base material may be degradable or non-degradable in a living body. When the base material is used as a biomaterial, it is advantageous to be degradable and absorbable in a living body. Such degradable base material may be constituted with a biodegradable resin.

Examples of the biodegradable resin include various kinds of resins such as said polysaccharides and their derivatives, polyesters such as homo or copolymers of hydroxycarboxylic acids (e.g. glycolic acid, lactic acid, 3-hydroxybutyric acid, 4-hydroxyburyric acid, 3-hydroxypropionic acid), specifically lactic acid-glycolic acid copolyester, copolyesters with hydroxycarboxylic acids, propionic acid or lactones (e.g. butyrolactone, caprolactone), etc.

These base materials may used alone or in combination of two or more of them. Also, two or more of the complex base materials may be used in combination.

The biomaterial of the present invention may be prepared by applying the polypeptide on the surface of a base material. The polypeptide may be applied to the portion of the base material to be applied to a living body (said portion including the site contacting to a body tissue or to body fluid or blood). In case of the base material being powdery or having a one-dimensional structure, the polypeptide may be applied to the entire of the base material. In case of the base material having a two-dimensional structure, the polypeptide may be applied onto at least one side of the surfaces. In case of the base material having a third-dimensional structure, the polypeptide may be applied to the portion to be applied to a living body such as the whole, inner or outer part of said base material. For example, a solution or suspension of the polypeptide may be coated or sprayed (or dipped) on the surface of the base material, followed by drying to give a biomaterial coated with the polypeptide on the surface. The porous base material may be dipped in the solution or suspension of the polypeptide to provide the biomaterial retaining the polypeptide therein.

When desired, the polypeptide carried on the base material may be cross-linked by the use of the same in a composition comprising a cross-linking agent, especially a physiologically acceptable crosslinking agent such as a dialdehyde (e.g. glyoxal, glutaraldehyde, succinaldehyde, malealdehyde), dextran dialdehyde or starch aldehyde. The amount of the cross-linking agent may be from 1 to 20 parts by weight, preferably from 1 to 10 parts by weight to 100 parts by weight of the polypeptide.

The amount of the polypeptide to be applied to the base material is widely varied with the configuration of the biomaterial and not limitative, but it may be usually from about 0.1 to 500 parts by weight (e.g. from 1 to 300 parts by weight), preferably from about 5 to 200 parts by weight (e.g. from 10 to 100 parts by weight) based on 100 parts by weight of the base material.

The composite of the invention may be used as such for a desired object. When used for a medical use, it is preferred to be subjected previously to disinfection or sterilization. For disinfection or sterilization, there may be adopted, for example, hot-steam sterilization, gamma-radiation sterilization, ethylene oxide gas sterilization, drug sterilization, and ultraviolet radiation sterilization, etc., among which hot-steam sterilization, gamma-radiation sterilization and ethylene oxide gas sterilization are preferred due to the high sterilizing efficiency and the less adverse effect on the composite.

The composite of the invention is suitable for an artificial bone material. Especially, the composite having a porosity of 0 to 50% has a dense quality and is suitable as a material for covering to support a defect of a bone of high strength bone. The composite having a porosity of 50 to 99% is suitable as a prosthetic material for a bone to which a light load is applied. The composite may be used in any shape such as prism, column or block. The artificial bone made of the composite may be provided with a hole for connecting it to a living bone, for example, by the use of a bolt and a nut. Further, the composite may be impregnated with such a promoter (e.g. bone-forming proteins, pone-forming peptides) for facilitating the invasion of cells therein.

In a preferred embodiment, the composite of the invention can provide such a biomaterial extremely excellent in processability as an artificial bone. The composite of the invention may be somewhat harder than collagen prior to precipitation of a calcium phosphate compound thereon but can maintain a feasibility of deformation like said collagen. For example, the composite is not collapsed on picking up with a tweezers and can be deformed without collapsing by applying a slight force thereto. On deformation with application of a force, the calcium phosphate compound precipitated on the composite is not exfoliated. Because of the mechanical property as above, the biomaterial comprising the composite of the invention may be freely deformed so as to adapt for the shape of a deficient bone in order to use as an artificial bone. Also, the biomaterial can be cut off easily with a scissors or the like, and therefore it may be shaped in an appropriate form, for instance, during a surgical operation. This is significantly advantageous in solving a technical problem present in a conventional artificial bone comprising a dense ceramic material, which is very hard and can be difficulty formed in an appropriate shape, particularly adaptable for the deficient site, during a surgical operation. In this specification, various amino acid residues are indicated by the following abbreviations:

Ala: L-alanine residue
Arg: L-arginine residue
Asn: L-aspargine residue
Asp: L-aspartic acid residue
Cys: L-cysteine residue
Gln: L-glutamine residue
Glu: L-glutamic acid residue
Gly: glycine residue
His: L-histidine residue
Hyp: L-hydroxyproline residue
Ile: L-isoleucine residue
Leu: L-leucine residue
Lys: L-lysine residue
Met: L-methionine residue
Phe: L-phenylalanine residue
Pro: L-proline residue
Sar: sarcosine residue
Ser: L-serine residue
Thr: L-threonine residue
Trp: L-tryptophan residue
Tyr: L-tyrosine residue
Val: L-valine residue Also, in this specification, the amino acids in a peptide chain are described in the common way, i.e. the amino acid residue at the N terminal being put on the left side and the amino acid residue at the C terminal being put on the right side.

EXAMPLE

The present invention will be hereinafter explained in more details by way of examples, but it shall not be understood that the present invention is limited to those examples.

Example 1

Synthesis of the Polypeptide

Using H-(Pro-Hyp-Gly)$_{10}$-OH, dimethyl sulfoxide, diisopropyl ethylamine, 1-hydroxybenzotriazole (HOBt) and 1-ethyl-3-(3-dimethylaminopropyl)-carbodiimide hydrochloride (EDC.NCl), a polypeptide was synthesized in the same manner as shown in Example 1 of JP-A-2003-321500. Specifically, H-(Pro-Hyp-Gly)$_{10}$-OH (5 mg) was suspended in dimethyl sulfoxide (1 mL), and the suspension was stirred at 20° C. To this mixture, diisopropyl-ethylamine (1.8 mM), 1-hydroxybenzotriazole (1.8 mM) and 1-ethyl-3-(3-dimethyl-aminopropyl)-carbodiimide hydrochloride (EDC.HCl) (3.4 mM) were added, followed by stirring at 20° C. for 48 hours to give the polypeptide. The obtained polypeptide solution was dialyzed in ultra-pure water to obtain the aqueous solution of the polypeptide. The molecular weight of the polypeptide was not less than about 2.0 kDa. The molecular weight was determined by the use of Gel Filtration LMW Calibration Kit and Gel Filtration HMW Calibration Kit (Amersham Biosciences) as the reference materials.

Example 2

Preparation of the Composite

Figure 1:
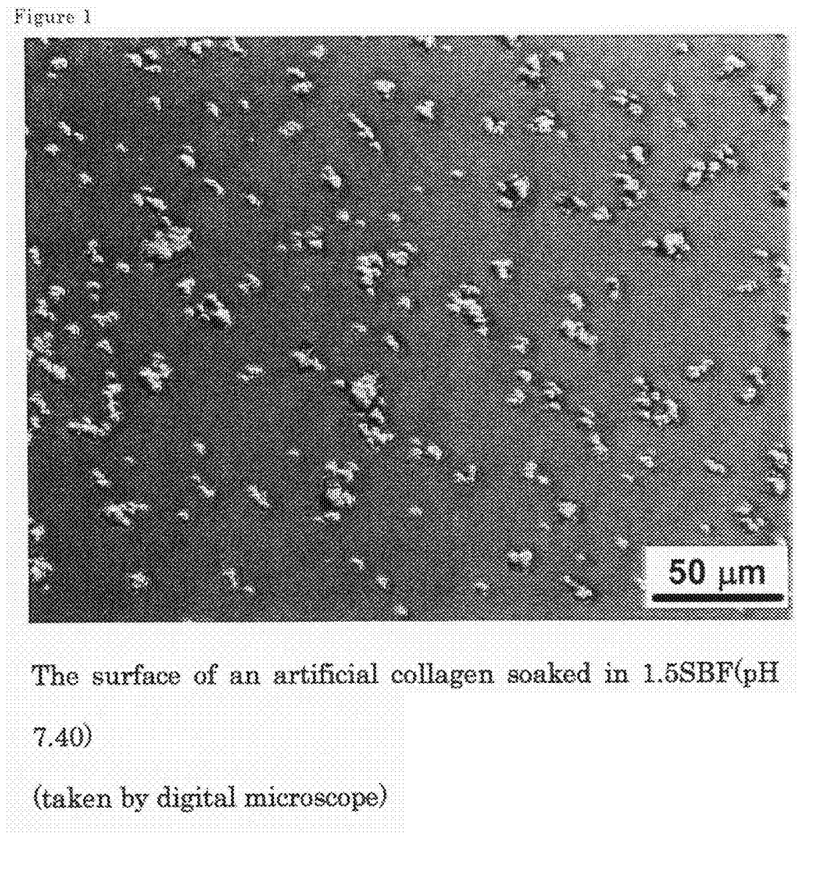
FIG. 1 is a photograph of a soaked film taken by digital microscope.
Figure 2:
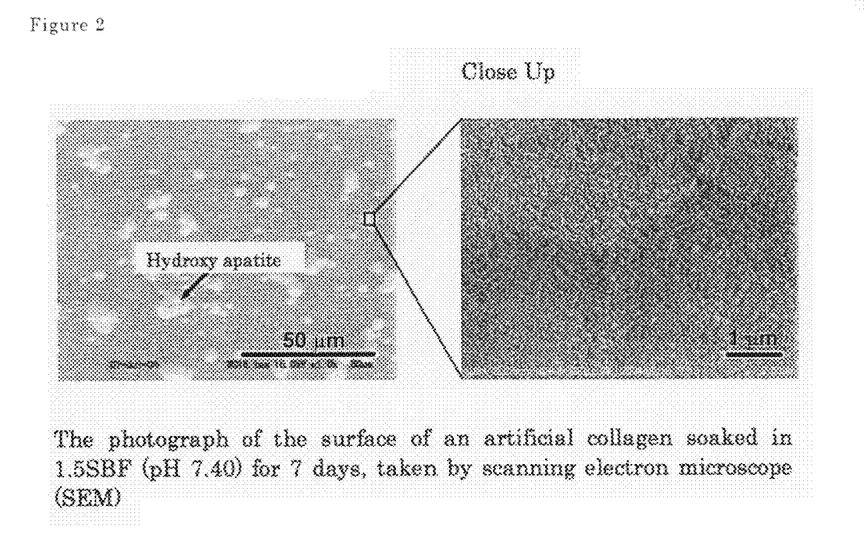
FIG. 2 is a photograph of a soaked film taken by scanning electron microscope (SEM)

An aqueous solution of the polypeptide obtained in Example 1(150 μL) was placed on a polystyrene-made petri dish and dried in air at room temperature for 24 hours to give a chemosynthetic collagen film (hereinafter referred to as "film before soaking"). An aqueous solution of $CaCl_2$ (1 mol/L) (5 mL) was added thereto and kept at 36.5° C. for 24 hours. After removing the $CaCl_2$ solution and washing 3 times with ultra-purified water (2 mL), the film was soaked in 1.5 SBF (pH=7.40) (10 mL) for 7 days to precipitate apatite on the surface of the film. Then, 1.5 SBF was removed, and the film was dried in air to give a desired composite film (hereinafter referred to as "film after soaking"). A photograph of the film after soaking was taken with a digital microscope VHX-100 (Keyence, VH-Z450 high performance lens) and is shown in FIG. 1. A photograph of the film after soaking was also taken with a scanning electron microscope (SEM, S-3500N, Hitachi) and is shown in FIG. 2.

Figure 3:
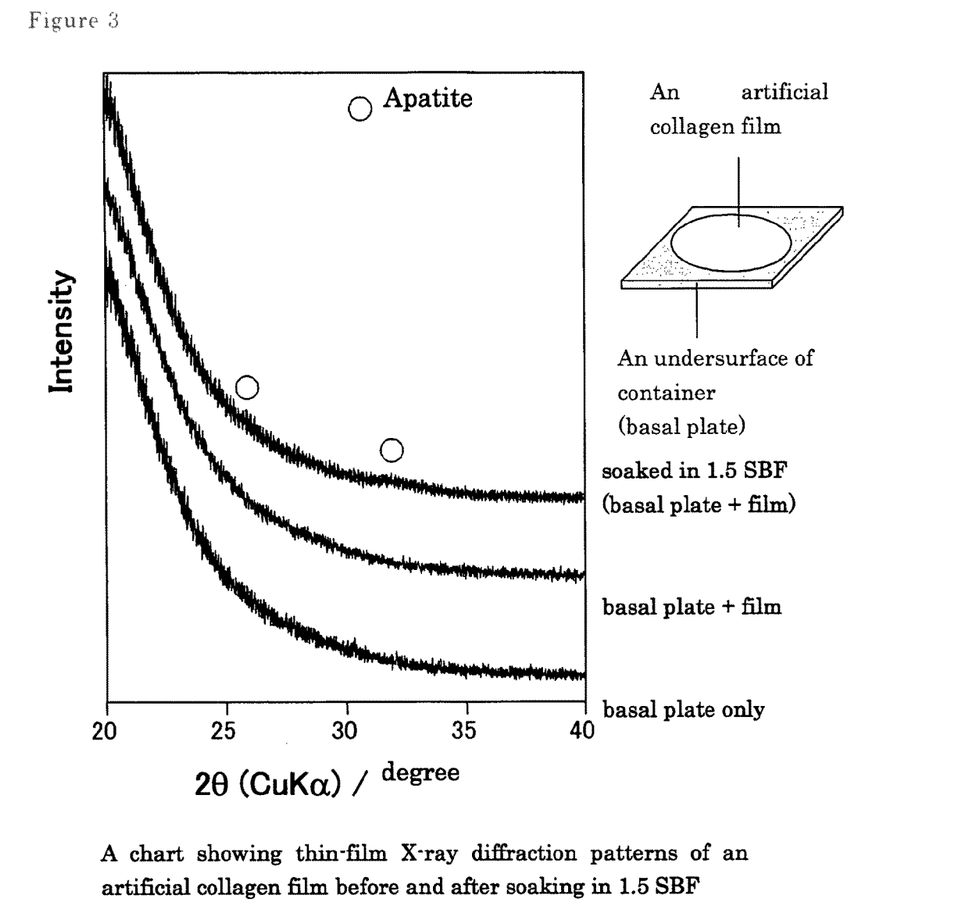
FIG. 3 is a chart showing thin-film X-ray diffraction patterns of a film before and after soaking.
Figure 4:
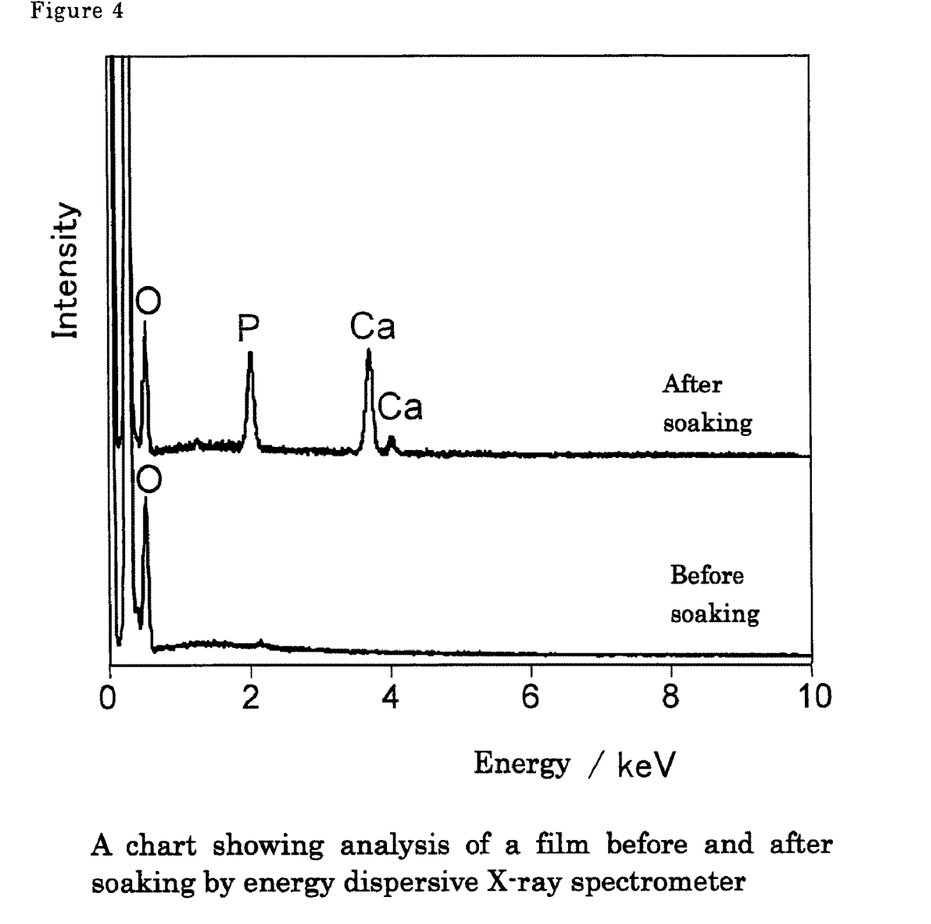
FIG. 4 is a chart showing elemental analysis of a film before and after soaking by energy dispersive X-ray (EDX) spectrometer.

The thin-film X-ray diffraction patterns of the films before and after soaking were determined with RINT2200V/PC-LR (Rigaku, X-ray source: Cu, energy: 40 kV/30 mA, X-ray incidence angle: 1°). The results are shown in FIG. 3. The films before and after soaking were analyzed with an energy dispersive X-ray (EDX) spectrometer (EMAX ENERGY EX-400, HORIBA Ltd.). The results are shown in FIG. 4. From FIGS. 1 to 4, the preparation of the chemosynthetic collagen/hydroxyapatite complex is confirmed.

Example 3

Synthesis of the Composite Having Silanol Groups

Figure 5:
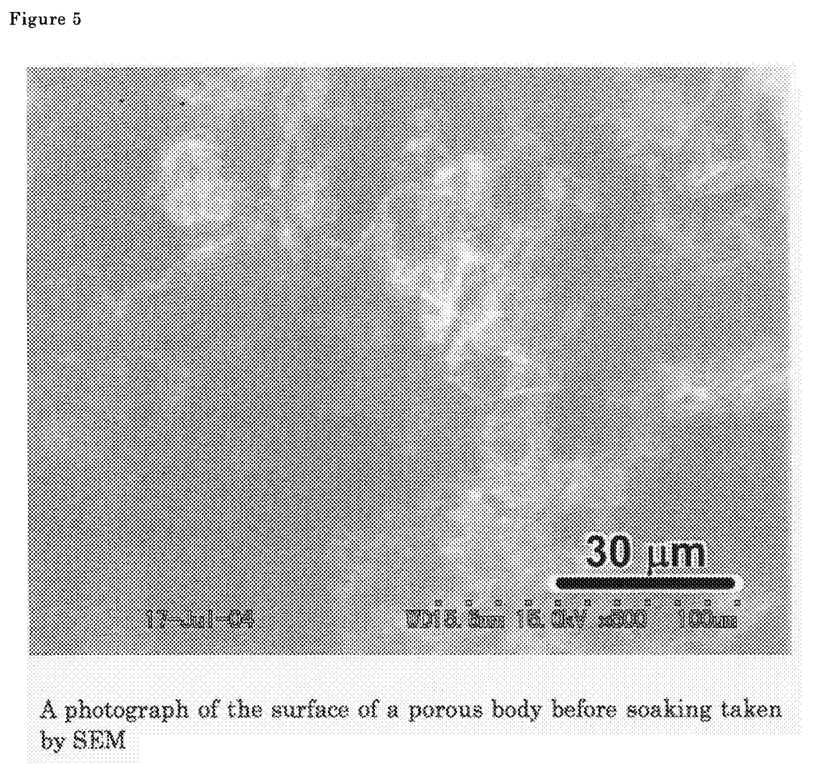
FIG. 5 is a photograph of the surface of a porous body before soaking taken by SEM.
Figure 6:
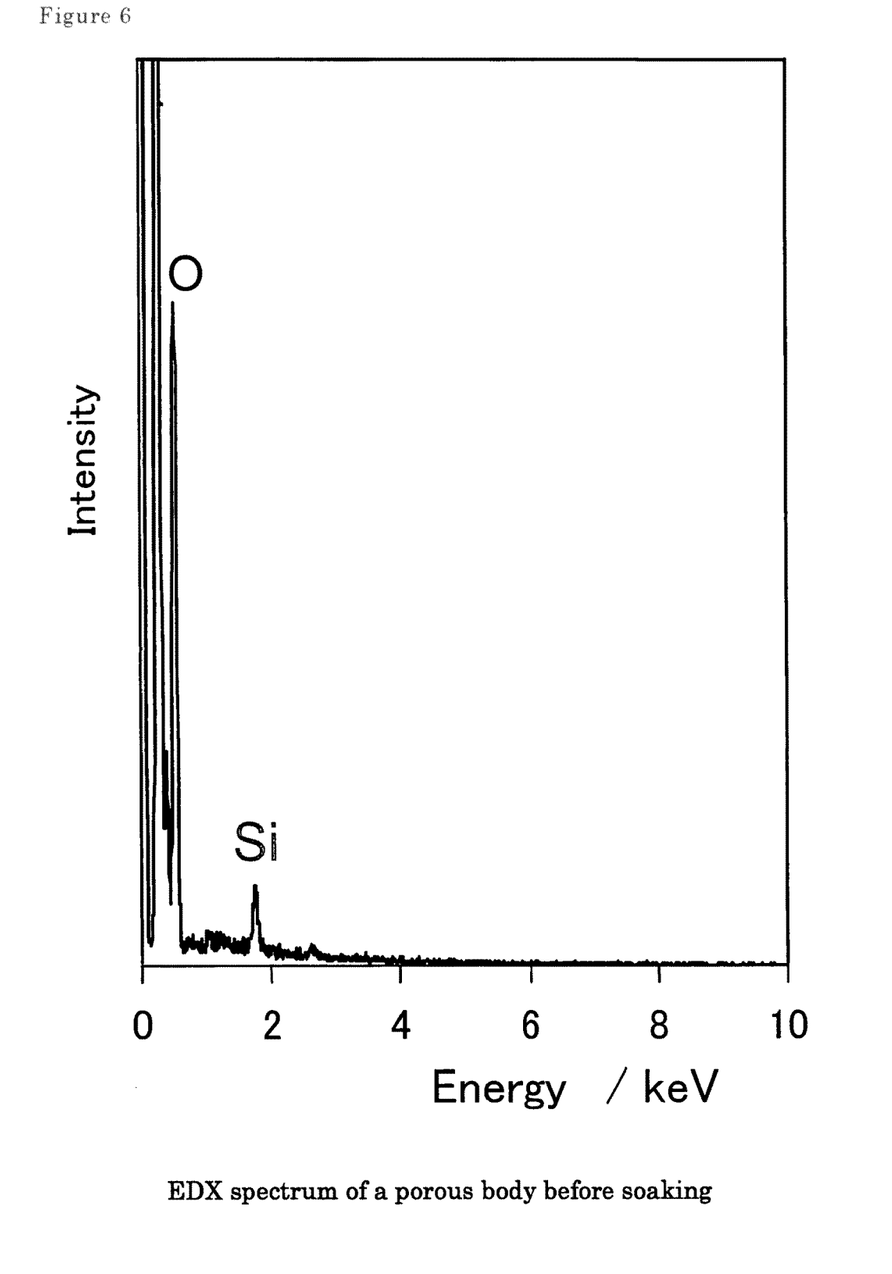
FIG. 6 is a chart showing EDX spectrum of the surface of a porous body before soaking.
Figure 7:
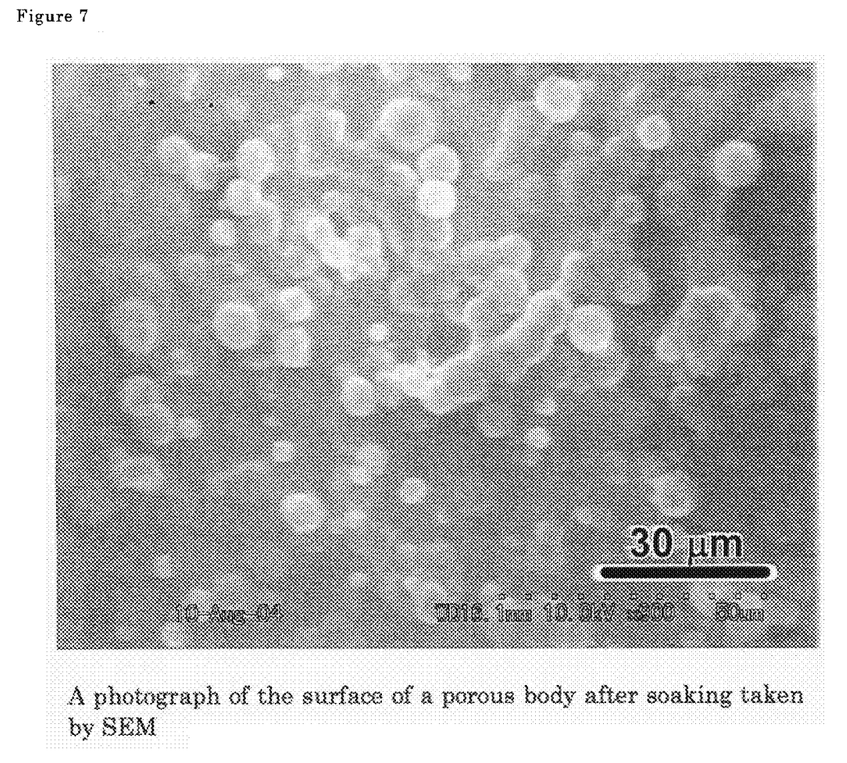
FIG. 7 is a photograph of the surface of a porous body after soaking.
Figure 8:
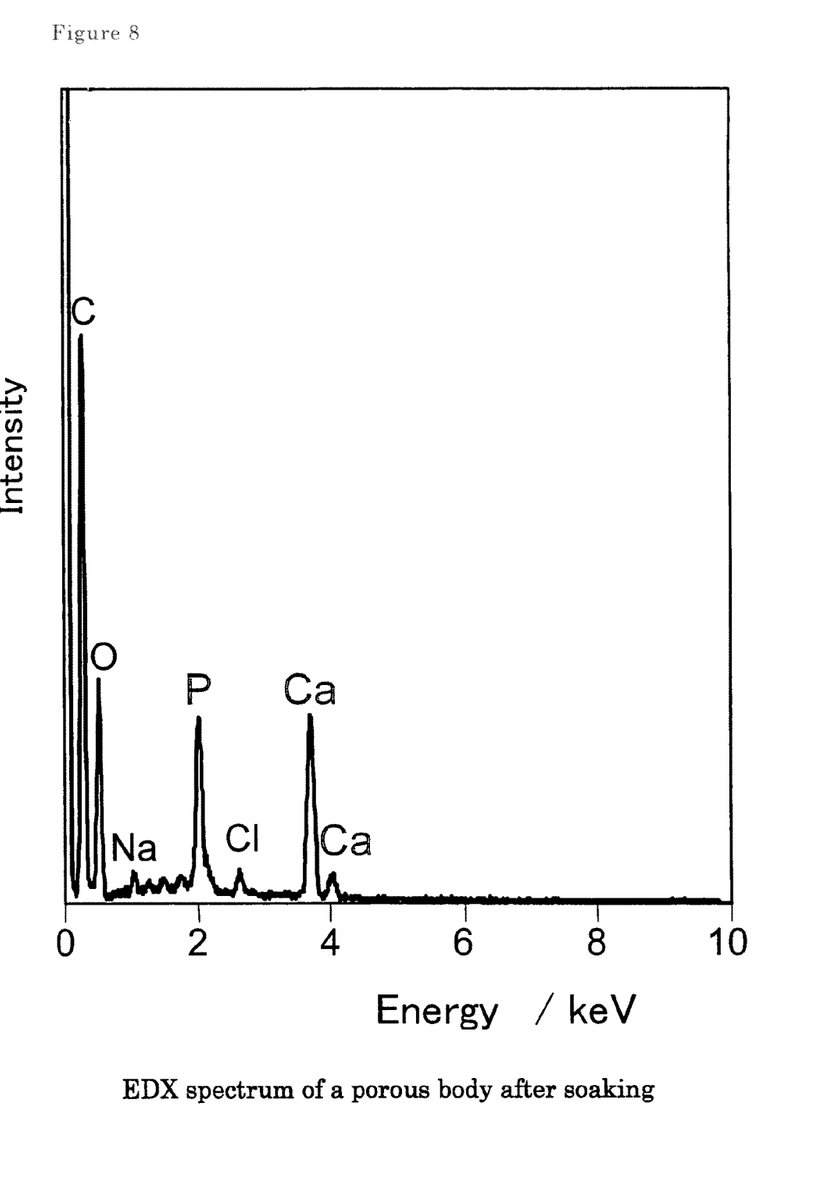
FIG. 8 is a chart showing EDX spectrum of the surface of a porous body after soaking.

The polypeptide aqueous solution obtained in Example 1 was freeze-dried and porous article was obtained. It was soaked in a THF solution of isocyanatopropyl triethoxysilane (IPTS, 10 vol %) (1 mL) and kept 36.5° C. for 24 hours. After washing with THF, the article was dried in air for 24 hours (hereinafter referred to as "porous article before soaking"). The SEM photograph and EDX spectrum of the surface of the porous article before soaking are shown in FIGS. 5 and 6, respectively. To the porous article, an aqueous solution of $CaCl_2$ (0.1 mol/L) (1 mL) was added, followed by keeping at 36.5° C. for 24 hours. After removing the $CaCl_2$ solution and washing with ultra-purified water, the article was soaked in 1 mL of 1.5 SBF (pH=7.25) for 7 days to precipitate apatite on the surface of the article. Then, 1.5 SBF was removed, and the article was dried by air to give the desired porous article (referred to as "porous article after soaking"). The SEM photograph and EDX spectrum of the surface of the porous article after soaking are shown in FIGS. 7 and 8, respectively. From FIGS. 7 and 8, the preparation of the chemosynthetic collagen/hydroxyapatite composite is confirmed. By comparing FIG. 2 with FIG. 7, it is understood that hydroxyapatite is deposited more on the chemosynthetic collagen having silanol groups.

The invention claimed is:

1. A biomaterial composite, which comprises a polypeptide and a calcium phosphate compound, said polypeptide comprising the units of Formulas (I) to (III):

[—(OC)—(CH$_2$)$_m$—CO)$_p$-(Pro-Y-Gly)$_n$-]$_a$    (I)

[—(OC)—(CH$_2$)$_m$—CO)$_q$-(z)$_r$-]$_b$    (II)

[—HN—R—NH—]$_c$    (III)

wherein;
m is an integer of 1 to 18;
p and q are each independently 0 or 1;
a is an integer of 1 to 10,000 and b and c are each independently an integer of 0 to 10,000; each of Ys is independently Pro, Hyp or a group of the formula:

wherein R' is H or C1-6 alkyl and X is a divalent group;
n is an integer of 1 to 20;
Z is an amino acid residue or peptide chain consisting of 1 to 10 amino acid(s);
r is an integer of 1 to 20;
R is a straight or branched chain alkylene group of 2 to 12 carbon atoms;
the molar ratio of a and b (a/b) is 100/0 to 30/70;
when p is 1 and q is 0, c equals to a;
when p is 0 and q is 1, c equals to b;
when p is 1 and q is 1, c equals to a+b; and
when p is 0 and q is 0, c is 0 in which at least one of Ys is a group of the formula:

2. The biomaterial composite according to claim 1, in which Z is an amino acid residue or peptide chain consisting of one or more of amino acids selected from Gly, Sar, Ser, Glu, Asp, Lys, H is, Ala, Val, Leu, Arg, Pro, Tyr and Ile.

3. The biomaterial composite according to claim 1, in which Z is an amino acid residue or peptide chain selected from Gly, Sar, Ser, Glu, Asp, Lys, Arg-Gly-Asp, Tyr-Ile-Gly-Ser-Arg, Ile-Lys-Val-Ala-Val, Val-Pro-Gly-Val-Gly, Asp-Gly-Glu-Ala, Gly-Ile-Ala-Gly, His-Ala-Val, Glu-Arg-Leu-Glu, Lys-Asp-Pro-Lys-Arg-Leu and Arg-Ser-Arg-Lys.

4. The biomaterial composite according to claim 1, wherein p, q and c are each 0.

5. The biomaterial composite according to claim 1, in which the polypeptide comprises the units of Formula (I'):

H-(Pro-Y-Gly)$_s$-OH    (I')

wherein s is an integer of 10 to 200,000 and Ys are each independently a group of the formula:

wherein R' is H or C1-6 alkyl and X is a divalent group.

6. The biomaterial composite according to claim 1, in which X is —CONHCH$_2$—, —CONHCH$_2$ CH$_2$—, —CONHCH$_2$ CH$_2$ CH$_2$—, —CONHCH$_2$ CH$_2$ CH$_2$ CH$_2$—, —CH$_2$ CH(OH)OCH$_2$—, —CH$_2$ CH(OH)OCH$_2$ CH$_2$—, —CH$_2$ CH(OH)OCH$_2$ CH$_2$ CH$_2$— or —CH$_2$ CH(OH)OCH$_2$ CH$_2$ CH$_2$ CH$_2$—.

7. The biomaterial composite according to claim 6, in which Ys in two different peptide units are combined together to form a siloxane bond.

8. The biomaterial composite according to claim 7, in which the calcium phosphate compound is $Ca_{10}(PO_4)_6(OH)_2$.

9. The biomaterial composite according to claim 8, in which the weight ratio of the polypeptide and the calcium phosphate compound is 1:9 to 9:1.

10. A polypeptide comprising the units of Formulas (I) to (III):

$[-(OC)-(CH_2)_m-CO]_p\text{-(Pro-Y-Gly}n\text{-}]_a$ (I)

$[-(OC)-(CH_2)_m-CO]_q\text{-(z)}_r\text{-}]_b$ (II)

$[-HN-R-NH-]_c$ (III)

wherein
m is an integer of 1 to 18;
p and q are each independently 0 or 1;
a is an integer of 1 to 10,000 and b and c are each independently an integer of 0 to 10,000;
each of Ys is independently a group of formula wherein R' is H or $C_{1-6}$ alkyl and X is a divalent group;
n is integer of 1 to 20;
Z is an amino acid residue or peptide chain consisting of 1 to 10 amino acid(s);
r is an integer of 1 to 20;
R is a straight or branched chain alkylene group of 2 to 12 carbon atoms;
the molar ratio of a and b (a/b) is 100/0 to 30/70;
when p is 1 and q is 0, c equals to a;
when p is 0 and q is 1, c equals to b;
when p is 1 and q is 1, c equals to a+b; and
when p is 0 and q is 0, c is 0.

11. The polypeptide according to claim 10, in which Ys in two different peptide units are combined together to form a siloxane bond.

12. A process for preparing the biomaterial composite according to claim 1, which comprises:
soaking a polypeptide comprising the units of Formulas (I) to (III)
in an aqueous solution of CaCl2 aqueous solution; and
soaking the polypeptide in a simulated body fluid (SBF) or concentrated simulated body fluid containing phosphate ion.

13. The biomaterial composite according to claim 1, wherein 3 said polypeptides form a collagen-like fiber of a triple-helical structure at their entire or parts.

14. The biomaterial composite according to claim 2 useful as an artificial bone, a dental implant, a bone reparative material, a bone filler, gnathic bone rebuilding material or an artificial joint fixation material.

15. The biomaterial composite according to claim 13 useful as an artificial bone, a dental implant, a bone reparative material, a bone filler, gnathic bone rebuilding material or an artificial joint fixation material.

16. A biomaterial composite for an artificial bone, which comprises a polypeptide as a polymer comprising the units of Formulas (I) to (III):

$[-(OC)-(CH_2)_m-CO]_p\text{-(Pro-Y-Gly}n\text{-}]_a$ (I)

$[-(PC)-(CH_2)_m-CO]_q\text{-(z)}_r\text{-}]_b$ (II)

$[-HN-R-NH-]_c$ (III)

wherein;
m is an integer of 1 to 18;
p and q are 0;
a is an integer of 1 to 10,000, b is an integer of 0 to 10,000 and c is 0;
each of Ys is independently Pro, Hyp or a group of the formula:

wherein R' is H or $C_{1-6}$ alkyl and X is a divalent group, in which at least one of Ys is a group of the formula:

wherein R' and X are as defined above;
n is integer of 1 to 20;
Z is selected from Gly, Sar, Ser, Glu, Asp, Lys, Arg-Gly-Asp, Tyr-Ile-Gly-Ser-Arg, Ile-Lys-Val-Ala-Val, Val-Pro-Gly-Val-Gly, Asp-Gly-Glu-Ala, Gly-Ile-Ala-Gly, His-Ala-Val, Glu-Arg-Leu-Glu, Lys-Asp-Pro-Lys-Arg-Leu and Arg-Ser-Arg-Lys;
r is an integer of 1 to 20;
R is a straight or branched chain alkylene group of 2 to 12 carbon atoms; and
the molar ratio of a and b (a/b) is 100/0 to 30/70;
wherein 3 said polypeptides form a collagen-like fiber of a triple-helical structure at their entire or parts; and wherein crystal of $Ca_{10}(PO_4)_6(OH)_2$ is precipitated on the surface of said collagen-like fiber.

17. A method for preparation of the biomaterial composite of claim 16, wherein said method comprises soaking a polypeptide in 1.0M of CaCl aqueous solution at 20 to 40° C. for 24 hours, and then soaking said polypeptide in 1.5 SBF containing 1.5 mM of phosphate ion at 20 to 40° C. for 7 days to give said biomaterial composite.

* * * * *